United States Patent [19]

Jungherr et al.

[11] Patent Number: 5,837,226
[45] Date of Patent: Nov. 17, 1998

[54] OCULAR MICROSPHERE DELIVERY SYSTEM

[75] Inventors: Lisa B. Jungherr, Los Altos; Thomas B. Ottoboni, Belmont, both of Calif.

[73] Assignee: Vitaphore Corporation C/O Integra Lifesciences Corp., Plainsboro, N.J.

[21] Appl. No.: 530,949

[22] Filed: Sep. 19, 1995

Related U.S. Application Data

[63] Continuation-in-part of Ser. No. 164,082, Dec. 8, 1993, abandoned.

[51] Int. Cl.⁶ ........................................................ A61K 9/50
[52] U.S. Cl. ........................ 424/78.1; 424/483; 424/78.04
[58] Field of Search ................................ 424/78.04, 78.1, 424/483

[56] References Cited

U.S. PATENT DOCUMENTS

| | | | |
|---|---|---|---|
| 4,847,091 | 7/1989 | Illum | 424/455 |
| 4,931,279 | 6/1990 | Bawa et al. | 424/427 |
| 5,288,503 | 2/1994 | Wood et al. | 424/497 |

FOREIGN PATENT DOCUMENTS

| | | |
|---|---|---|
| 261 693 | 9/1987 | European Pat. Off. . |
| 0 294 103 | 12/1988 | European Pat. Off. . |
| 0 349 453 | 1/1990 | European Pat. Off. . |
| 87/03197 | 6/1987 | WIPO . |
| 9111871 | 7/1992 | WIPO . |
| 92/11871 | 7/1992 | WIPO . |
| 93/17716 | 9/1993 | WIPO . |

*Primary Examiner*—Peter F. Kulkosky
*Attorney, Agent, or Firm*—Campbell & Flores LLP

[57] ABSTRACT

A sustained release drug delivery composition and a method of making same are provided which comprises microspheres containing a pharmaceutically active agent, a core of a ion-exchange resin and a polymeric coating completely surrounding the core wherein the coating is water-insoluble and hydrolytically stable in physiological environments. The coating is non-erodible in physiological environments and is characterized by a diffusion constant suitable for the pharmaceutical agent to diffuse from the core to an aqueous environment at a predetermined release rate.

2 Claims, 1 Drawing Sheet

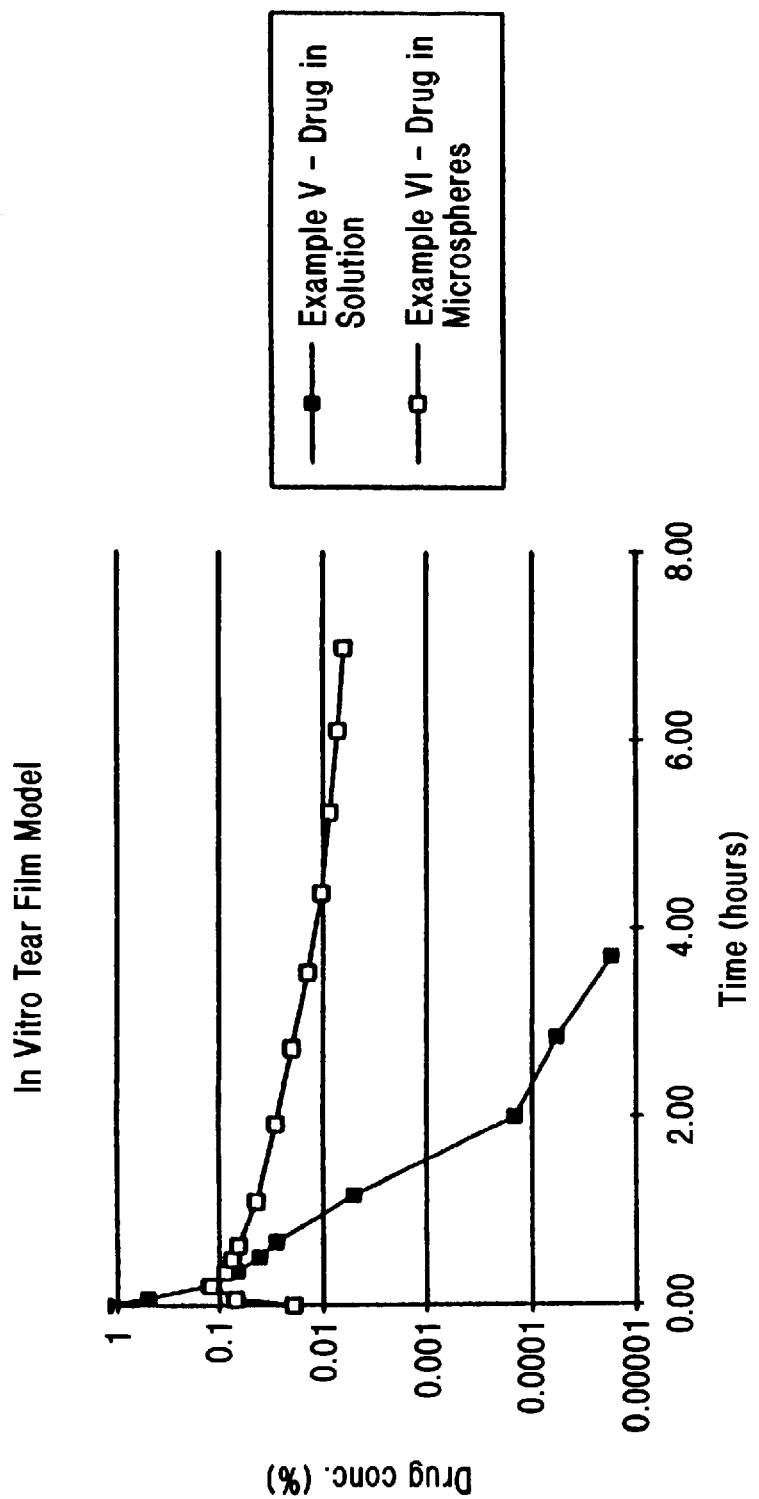

OCULAR MICROSPHERE DELIVERY SYSTEM

CROSS REFERENCE TO RELATED APPLICATIONS

This is a continuation-in-part U.S. patent application Ser. No. 08/164,082, filed on Dec. 8, 1993, now abandoned.

FIELD OF THE INVENTION

The present invention is directed to systems for topical drug delivery using microspheres with diffusion-controlled drug release. The present invention is particularly directed to ocular delivery systems.

BACKGROUND OF THE INVENTION

The present invention is advantageous over the following methods of ocular drug delivery.

Eyedrop solutions are inefficient because the solution will drain through the nasal lacrimal duct into the nasal cavity creating systemic drug exposure. Thus, solutions with relatively high concentrations are required, usually in the range of about 0.5 to 2% weight by volume, in order to provide an effective dose at the target site. Prolonged contact of the therapeutic agent with the eye is of course inconvenient when eyedrops must be frequently applied. In some instances, due to the high dosages which are required for use of drops, there can be systemic toxic side effects. For all of the above reasons, eyedrops cannot be continuously added to the eye as a means of prolonged topical ocular delivery.

Ointments and gels as drug delivery systems may be used for prolonged delivery because of their slow dissolution. However, since they are generally uncomfortable and blur the vision, they can only be S used when the subject is inactive.

Ocular inserts such as those disclosed in U.S. Pat. Nos. 3,845,201, 4,164,559 or 4,179,497, allow prolonged delivery of a drug released from the insert. However, patient compliance with proper use of the insert is low because the inserts are difficult to place in the eye, especially for elderly persons. Furthermore, retention of the insert in the eye can be a problem, and they produce an uncomfortable foreign body sensation in the eye.

Therapeutic suspensions, as opposed to eyedrop solutions, discussed above, may be used for compounds having low solubility, since the rate of release of the drug is related to its solubility in the eye. The primary application of therapeutic suspensions for the eye has been essentially limited to low-solubility steroids.

Microencapsulated drugs may be delivered to the eye, but preparation of the drug-encapsulating microspheres is complicated because the drug must be placed in the microsphere during the fabrication of the microsphere. Furthermore, normally the release of the drug from the microsphere is controlled by placing the microsphere in an aqueous system. Therefore, the microsphere can only be mixed with the delivery vehicle just prior to use, which makes its use inconvenient.

U.S. Pat. No. 4,865,846 to Kaufman discloses an ophthalmic drug delivery system in which there is a carrier in a bio-erodible material so it appears that the drug is released by bio-erosion.

Published PCT application W092/11871, published Jul. 23, 1992, discloses a sustained release pharmaceutical compound delivery composition wherein an ion exchange resin particle is loaded with releasably bound pharmaceutical compounds prior to incorporation into an erodible polymeric matrix to form microparticles. A disadvantage of the microparticles disclosed in this application is the coating of the resin particle is erodible therefore the drug apparently must be loaded into the ion exchange resin before the erodible coating is placed thereover. Therefore, since the complete microsphere, comprising the ion exchange resin core, erodible coating and drug-loaded into the core, is made after the microsphere has been loaded with the drug, the microsphere can only be sterilized with the drug present in the microsphere. Accordingly, exposure to typical sterilization conditions of heat or irradiation can cause reactions which adversely affect the drug and/or the microsphere.

The present invention is directed to an ocular delivery system comprising microspheres which avoids these disadvantages and which provides further advantages. One of the advantages of the present invention is that the drug can be loaded into the microspheres after the microspheres have been formed, thus providing the opportunity for an intermediate sterilization step for the microspheres. Sterilization can cause side reactions and can typically result in decomposition of the drug if the microspheres are sterilized when they contain the drug.

The microspheres according to the present invention comprises an ion exchange resin core which actively binds to the drug. One can load the microspheres with the drug at a concentration which is higher than the concentration of the drug in the surrounding liquid carrier. Furthermore, the microspheres according to the present invention are essentially non-irritating to the eye because of their small particle size.

Furthermore, by providing a core of ion exchange resin which has a high drug binding capacity and surrounding this core with a polymer coating which controls drug release by diffusion, there is control over the drug release rate from the microspheres, thus providing versatility for use with a wide range of therapeutic agents.

It is a particular advantage of the present invention that the drug can be loaded into the microsphere subsequent to the sterilization of the microsphere materials, which is a feature not believed to be shown in the prior art.

SUMMARY OF THE INVENTION

The present invention provides a sustained-release drug delivery composition comprising a carrier and microspheres containing a pharmaceutically-active agent. The microspheres comprise a core which is an ion exchange resin and a polymeric coating completely surrounding the core wherein said coating is water-insoluble, hydrolytically stable in aqueous suspensions and is characterized by a diffusion constant for the agent suitable for diffusion of the agent from the core to the aqueous environment at predetermined release rate. By "hydrolytically stable" it is meant that the coating does not erode or decompose under constant exposure to the aqueous environment of the eye for at least the period during which the drug is being released from the microspheres. Typically, drug will be released for up to about 8 hours, and the microspheres will not decompose for at least that period. Preferably, the microspheres will not decompose for at least twenty-four hours. Shelf-life for the microspheres in suspension will typically be over one month. The ion exchange resin core preferably comprises particles having an average diameter of less than about 5 microns and the microspheres preferably have an average diameter in the range of around 5–20 microns. Coatings are preferably polymers characterized by a diffusion constant in the range of $10^{-7}$ to $10^{-12}$ cm$^2$/sec for the agent.

BRIEF DESCRIPTION OF THE DRAWING

In the accompanying FIGURE, there are shown graphs of the concentration of drug vs. time in an eluate from a reservoir containing an aqueous solution of drug, and from a reservoir containing microspheres which contain the drug.

DESCRIPTION OF THE PREFERRED EMBODIMENTS

The drug delivery system according to the present invention comprises a carrier and microspheres. The microspheres are not necessarily spherical, but should have an average diameter, regardless of their shape, of preferably less than or equal to about 20 microns, since particles of these dimensions do not irritate the eye. The microspheres will be suspended in a carrier (pharmaceutical vehicle) suitable for contacting the eye surface and which may also contain the drug. The drug contained in the vehicle may be the same drug contained in the microspheres, may be a different drug, or may be a combination of drugs intended for delivery upon contact of the vehicle with the eye. The vehicle is aqueous, preferably a buffered solution isosmotic with tears, such as a mannitol solution.

The composition preferably contains osmotic agents sufficient to render the composition acceptable to the eye, particularly osmotic agents which provide an osmotic pressure identical to or close to the osmotic pressure of tears. Exemplary osmotic agents are sodium chloride, lithium chloride, potassium sulfate, sodium sulfate, calcium sulfate, magnesium sulfate, mannitol, glucose, sucrose, and the like. Preferably, soluble non-ionic compounds such as mannitol are used to achieve isotonicity without raising the ionic strength of the suspension. Preservatives and antibacterial agents such as benzalkonium chloride and phenylethyl alcohol may also be utilized in the vehicle in order to provide a suitable shelf life of the composition prior to use. The preservatives and antibacterial agents are compatible with the pharmaceutically active agent, non-toxic, non-irritating to the eye and other tissues. Typical concentrations of preservatives and antibacterial agents are 0.0005% to 0.005% wt. by volume in the vehicle. Other typical optional additives include viscosity enhancers such as polyethylene glycol, polyvinyl pyrrolidone, and carboxymethyl cellulose. These agents reduce the rate at which the composition leaves the eye and can enhance comfort for the user.

It may be desirable in some instances to enhance the residence time of the microspheres in the eye to prolong the treatment and release of the drug. In such instances the vehicle may contain materials which form a gel when placed in contact with the physiological environment of the eye in tears. Such materials are known and include polycarboxylic functional polymers, such as polyacrylic acid (such as, Carbopol™, Polycarbophil™ (B.F. Goodrich)); and polysaccharides such as gellan gum. Alternatively, a gel coating may be polymerized on the surface of the microspheres or a second mucoadhesive coating may be applied over the microspheres whereby the microspheres will adhere to the surface of the eye. Thus, while the microspheres which have a mucoadhesive character may be swept out of the eye along with a normal turnover of the mucin (approximately every 24 hours) they will remain in the tear fluid for a period of time which is sufficient to complete release of the drug. Since the ocular mucin is primarily composed of glycoprotein, a protein backbone with covalently bound oligosaccharide side chains, the surfaces of the microspheres can be made to contain, by either an overcoating or by surface modification to expose or attach appropriate groups, functional groups capable of hydrogen bonding (e.g. carboxyl, amide, hydroxy, amine, etc.), will allow for mucoadhesion. Mucoadhesion primarily involves hydrogen bonding, van der Waals, electrostatic, and hydrophobic forces. Since the strongest of these forces is hydrogen bonding, functional groups capable of hydrogen bonding to the oligosaccharide chains in the mucin will have mucoadhesive properties.

The drugs which may be utilized in accordance with the present invention include, but are not limited to, ophthalmic drugs, such as antibiotics such as tetracycline, neomycin, polymyxin, gramicidin, gentamicin, tobramycin, trimethoprim, choramphenicol, bacitracin, erythromycin; antibacterials such as sulfonamides, sulfacetamide, sulfamethizole and sulfisoxazole; antivirals; anti-inflammatories such as hydrocortisone, dexamethasone, fluocinolone, fluorometholone and triamcinolone; cholenergics and anticholinesterases such as pilocarpine, eserine salicylate, carbachol, and demecarium bromide; mydriatics such as atropine sulfate, scopolamine, tropicamide and hydroxyamphetamine; sympathomimetics such as epinephrine; beta-blockers, such as betaxolol, levobunolol, metipranolol, adaprolol, alprenoxime, carteolol, and timolol; and other drugs such as acetazolamide, apraclonidine, methazolamide, $PGF_2$-alpha-IE, $PGA_2$-IE, Sulprostone (a prostaglandin), and verapamil.

An advantage obtained by the present invention is that it provides a reliable system for extended delivery of drugs to the tear film and other mucosal surfaces in a convenient drop form as a suspension of microspheres. There is no blurring of the vision as in the case of ointments or gels, and it is comfortable to the eye compared to an ocular insert.

The microspheres used according to the present invention have a binding affinity with a charged (ionic) drug such that the microspheres will actively take up the drug. The binding affinity of a particular macromolecule for a drug can be determined as follows. The amount of bound drug and free drug are determined.

Bound drug=total amount of drug found in microspheres which are contacted with a solution of the drug and allowed to equilibrate minus volume of solution absorbed by the polymer sample times the concentration of drug in the remaining unabsorbed solution Then, $$\text{Binding afffinity} = [\text{Bound drug}]/[\text{Free drug}]$$
$$= \frac{[\text{Bound drug}]}{[\text{Total Drug}] - [\text{Bound drug}]}$$

Generally, a higher binding affinity provides a longer sustained release of the drug. Preferred microspheres have binding affinities over 0.8, and preferably 1.0 and higher, as measured by the method above. Particularly useful binding affinities are in the range of 1.0 to 30.0. It will be appreciated that if measured in the eye, the observed binding affinity will be lower due to the higher ionic strength of the environment.

An advantage of the microspheres according to the present invention is that when they are placed in a solution containing a charged drug they will actively take up the drug if the ion exchange resin at the core of the microsphere contains groups of the opposite charge to that of the drug. Typically, the microspheres will bind 90–95% of the total drug in the original solution. It will be appreciated that the bound fraction depends on the particular drug, concentration and amount of ion exchange resin. The mechanism of action is by ion-pairing typical of operation of ion-exchange resins. Therefore, the drugs to be used in accordance with the invention are prepared in an ionic form, which can be accomplished generally by formulation conditions which allow for the formation of ionic species. For example, the drug may be precipitated as a hydrochloride salt, if an amine is present in the drug. If the drug contains acid groups, it may be prepared as a sodium, lithium, etc., salt of the acid. Typically a low ionic strength solution of the drug is contacted with the microspheres to maximize the drug binding of the material. Then, the suspension is made isotonic prefereably using soluble non-ionic compounds such as 5 mannitol.

The microspheres according to the present invention comprise a core of ion exchange material. Typically the ion exchange material, if not available in the preferred sizes of about 5 microns or less in diameter, will be ground by appropriate methods to obtain the desired sizes. It is not necessary that the particles be essentially spherical in shape. Typically if the drug to be bound is a cation, the ion exchange resin will be anionic and if the drug to be bound is anionic, the ion exchange resin will be cationic. While not intending to be limited by the following, a typical range of ion exchange resins are Amberlite IR-20, Amberlite XE-69 and Amberlite IRP69, which are gel-type divinylbenzene, sulfonic acid cation exchange resins. Other ion exchange resins include those based on methacrylic, acrylic and phenol formaldehyde copolymers, cellulosic or dextran polymers or inorganic matrices such as a silica gel containing ionic groups. Generally, those types of ion exchange resins suitable for use in ion exchange chromatography are suitable for use in the controlled release microsphere drug preparations according to the present invention. Typical ion exchange resins are described by H. F. Walton in "Principles of Ion Exchange" (pages 312–343) and "Techniques Applications of Ion-Exchange Chromatography" (pages 344–361), in *Chromatography,* (E. Heftmann, ed.) Van Nostrand Reinhold Company, New York (1975), incorporated by reference herein. The exchange resins typically have exchange capacities above about 4 meq/gram, and usually in the range of 4–8 meq/g.

The microspheres will typically comprise a single ion exchange resin particle as the core, coated with the diffusion polymer, however, it is also within the scope of the present invention to provide a microsphere comprising a plurality of ion exchange particles bound together and coated with the diffusion polymer to comprise a single microsphere. The particles may be irregular or spherical, since the particle shape is not critical to the present invention.

The ion exchange material is typically a cross-linked ion polymer such as those described above. The diffusion controlling polymer which comprises a coating should be water insoluble and preferably have a diffusion constant of $10^{-7}$ to $10^{-12}$ cm$^2$/sec for the pharmacological agent bound by the ionic polymer. The diffusion constants can be readily determined by kinetic transport experiments described in texts such as *Controlled Release of Biologically Active Agents,* Baker, Richard, John Wiley & Sons (1987), Chapter 2.

The ion exchange resins typically possess negative charge since most pharmaceuticals are positively charged. If the drug is cationic then the ion exchange resin must contain anionic groups such as carboxylate, sulfonate or sulfate groups. The ionic exchange resin is preferably highly cross-linked material with a high charge density such as those described above. Since the microparticles according to the present invention are non-erodible in the physiological environment, the ion exchange resin should be insoluble in water although a small degree of swelling in water is tolerable. Preferably the particle size of the ionic resin core is less than about 5 microns.

The ion exchange core is surrounded by a water insoluble, hydrolytically stable polymeric material which forms a coating having a diffusion for the pharmaceutical agent sufficient to allow the agent to be released into the ocular environment at the desired rate. While not intending to be limited by the following, the polymer coating may be a cellulose derivative, a polycaprolactone polymer or copolymer, a polyurethane polymer or copolymer, a methacrylate polymer or copolymer, a polyester polymer or copolymer, and the like, as long as the coating is essentially non-erodible in the physiological environment of the eye. This means that the polymer coating must be water-insoluble and hydrolytically stable. It is important that the coating be non-erodible in the environment of the eye so that the release of the drug is controlled by diffusion through the coating rather than by erosion of the coating which would thus expose the core directly to the environment and possibly release the drug at a higher than desired rate.

The diffusion polymer includes such materials as cellulose derivatives such as ethylcellulose, cellulose acetate, cellulose propionate, cellulose acetate-propionate, etc., and such materials as Eudragit™ RL-100 and RS-100 (ammonio methacrylate copolymers manufactured by Rohm Pharma), polycaprolactones and polycaprolactone copolymers, polyesters such as ethyl vinyl acetate copolymers, polyurethanes and polyurethane copolymers, and the like.

The microparticles according to the present invention are formed by solvent evaporation, spray drying or any other technique for forming microspheres.

Typically the ion exchange resin material, if not initially available in the desirable size range, is milled to the desired particle size. After washing and drying of the ground particles of the ion exchange resin, they are dispersed in an appropriate organic solvent such as methylene chloride to form dispersions containing preferably between about 50 to 400 mg of ionic exchange resin per gram of solvent. A useful dispersion will contain about 220 mg of ion exchange resin per gram of methylene chloride. A solution of the diffusion polymers is made by dissolving the polymer in the organic solvent. Typically, a solution of 5 to 50 percent of the polymer in solvent is prepared. A particularly useful solution is a 30% (weight by volume) solution of polymer in methylene chloride. Typically, a 20% (by weight of the ion exchange resin) dispersion is mixed with an equal weight of organic solvent and about 4X the weight of the polymer-containing solution. After the mixture is uniformly dispersed, it is added to a surfactant such polyvinyl alcohol in aqueous phase and then emulsified. After adding more surfactant and more solvent, the emulsion is stirred and the solvent is allowed to evaporate, yielding the coated microparticles.

The microparticles may also be directly formed using spray drying technology. For example, an aerosol of ionic exchange resin particles suspended in a solution of the polymer coating can be introduced into a stream of hot air whereby the solvent is quickly evaporated. The dried particles are collected using, for example, a cyclone separator.

It will be realized that other surfactants besides PVA may be utilized such as fatty alcohol, ethers or polymers. Typical surfactants include Pluronics®, Spans® and Tweens® of hydrophilic-lipophilic balance (H.L.B.) value of 1 to 25, glycol monolaurate, polyoxy-ethylene sorbitan monooleate (Tween 80), and the like. The proportion of surfactant to ion exchange particles and coating polymer depends upon the types and amounts of the other components present, and efficiency of utilization of the particle polymer starting materials may be maximized by selecting optimal proportions. Typical surfactant amount are about 1% to 10% by weight in water.

According to the present invention the drug is loaded after the fabrication of the microspheres simply by combining a solution of the drug with the microspheres. The microspheres will rapidly bind the drug present in solution. Drug release will be slow based on the diffusion control release through the coating. This is an improvement over methods of encapsulating drugs in microspheres requiring that the drug be incorporated in the microsphere during the fabrication of the microsphere. Furthermore, according to such prior art methods, the microsphere must be sterilized when it contains the drug, thereby increasing the chances of altering the drug chemically, or inducing reactions which bind the drug to the substances in the microsphere. Other methods in the art which utilized microspheres to encapsulate drugs rely on utilizing the particles as sponges whereby the concentration of the drug in the microsphere cannot exceed the concentration in the solution. According to the present invention, it is contemplated that the concentration of the drug within the microsphere which contains a ion exchange resin core will be in the range of about 20 to 100 times higher than a concentration of the drug in the surrounding solution.

While not intending to be bound by any theory, when the drug-loaded microspheres are placed in the eye, the release of bound drug is initiated by ion exchange with the ionic species naturally present in drug release is controlled by diffusion from the core of the microsphere through the polymer layer. Due to the affinity of the drug for the ion exchange resin core and due to the diffusion limitation of the surrounding polymer, the drug release is prolonged, thus providing drug for a longer period of time in the eye than that which is achievable by a single application of an eyedrop solution. Furthermore, since the microspheres do not erode within the eye, essentially all of the drug may 5 the tear. The rate of the be released from the microspheres under conditions that do not degrade the microsphere.

Particular benefits achieved by the present invention are that there is a reliable delivery of drug to the tear film which can be delivered to the eye in a suspension as a convenient drop form. There is essentially no blurring of vision and the material is comfortable within the eye. The particles are not erodible but they will be swept out of the eye with normal mucin turnover. Finally, the microspheres can be sterilized in absence of the drug. The drug, according to the present invention, may be incorporated into sterile microspheres by combining them with a sterile solution of the drug prepared by standard techniques, such as by sterile filtration.

Having described the preferred embodiments of the invention, the following examples are provided by way of illustration and are not intended to limit invention in any way.

EXAMPLE I

Preparation of Materials for Drug Delivery Microspheres

The following procedure is used to prepare ocular drug-delivery microspheres. These microspheres are solid particles of about 5–10 $\mu$m comprising a core of ion-exchange resin in a polymer matrix. The core provides binding of ionic drugs, and the polymer shell provides a diffusion barrier to produce slow, controlled release of the drug.

Materials

1. RP-69—Amberlite cation exchange resin, Rohm & Haas, Philadelphia Pa.
2. Eudragit RL-100—Ammonio methacrylate copolymer, Rohm Tech, Malvern Mass.
3. Airvol 203—Polyvinyl alcohol, Air Products & Chemicas Inc., Allentown Pa.
4. Methylene Chloride or Ethyl Acetate
5. Deionized Water Preparation A. IRP-69 is milled to reduce the particle size from about 100–500 $\mu$m to about 2–5 $\mu$m:
  1. Fill a milling jar (US Stoneware 000, capacity ~330 ml) about half full with milling medium (~500 g). Add 40 ml IRP69 powder and 60–80 ml DI water. Place the mill on a bottle roller and mill for about 4–5 days. The powder will reach a terminal particle size distribution.
  2. Spray-dry the IRP solution to remove water.
  3. Add the dry IRP to the appropriate solvent; mill briefly to disperse the IRP.

B. A solution of 4 or 8% PVA in DI water is prepared: Combine PVA and water in a large bottle. Mix with a stir-bar until the PVA is dissolved. Filter the solution through a 20 $\mu$m nylon mesh to remove undissolved PVA particles.

C. A solution of Eudragit in solvent is prepared: Combine Eudragit and solvent in a bottle. Place on a bottle roller and roll until the polymer is dissolved.

EXAMPLE II

Preparation of Encapsulated Microspheres From Methylene Chloride Solution

The following were combined and mixed well:

20 g of 30% Eudragit RL-100 in methylene chloride ($CH_2Cl_2$).

5 g of 220 mg/g IRP-69 in methylene chloride.

5 g of methylene chloride.

This dispersion was added to 25 ml of 4% PVA solution in DI water and vortexed thoroughly. The mixture formed a bicontinuous emulsion which is thick and white.

400 ml 4% PVA in DI water was presaturated with 5 ml $CH_2Cl_2$. While the solution was magnetically stirred at high speed, the bicontinuous emulsion was added. The stirring continued for 6 hours or overnight to allow the solvent to evaporate.

The microspheres were isolated by centrifugation. The isolated microspheres were resuspended into 30 ml of DI water and isolated by centrifugation. This procedure was repeated 3 more times. The concentrated slurry may be sealed in a vial and sterilized by exposure to ionizing radiation.

EXAMPLE III

Preparation of Encapsulated Microspheres From Ethyl Acetate Solution

The following were combined and mixed well:

20g of 30% Eudragit RL-100 in ethyl acetate.

5g of 220 mg/g IRP-69 in ethyl acetate.

5g of ethyl acetate.

This dispersion was added to 25 ml of 8% of PVA solution in DI water and vortexed thoroughly. The mixture formed a bicontinuous emulsion which is thick And white.

A sample of 400 ml of 8% of PVA in DI water was presaturated with 5 ml ethyl acetate. While the solution was magnetically stirred at high speed, the bicontinuous emulsion was added. The stirring continued for 6 hours or overnight to allow the solvent to evaporate.

The microspheres were isolated by centrifugation. The isolated microspheres were resuspended into 30 ml of DI water and isolated by centrifugation. This procedure was repeated 3 more times. The concentrated slurry may be sealed in a vial and sterilized by exposure to ionizing radiation.

EXAMPLE IV

Drug Loading of Hydrogel Microspheres

Three hundred μg of concentrated slurry, prepared as described in Example II, was added to 1 ml of a 0.9% timolol solution. The solution was gently mixed for 1 hour. The resulting solution contains drug loaded microspheres. The amount of the timolol incorporated into the microspheres was determined by measuring the concentration of timolol in the aqueous portion of the microsphere dispersion and comparing that to the amount of timolol added to the solution, the difference being the amount incorporated in to the microsphere.

EXAMPLE V

An In Vitro Tear Film Model

A 500 ul reservoir with 2 openings on opposite sides was filled with an aqueous solution of timolol. The reservoir contained a 0.45 μm filter between-the two openings. The inlet was connected to a peristaltic pump via silicone tubing. The reservoir was perfused with physiological saline solution and the eluate was collected. The rate of perfusion was adjusted such that the rate of elimination of timolol from the reservoir was comparable to the rate of elimination of a timolol from the tear film of the eye. This rate of perfusion was used for all concentration of timolol subsequent experiments. The in the eluate was determined by W spectroscopy and graphed versus time. The results are presented in the FIGURE.

EXAMPLE VI

In Vitro Release of a Drug From Encapsulated Microspheres

A dispersion of timolol loaded microspheres, prepared as described in Example II, was placed into a 500 μl reservoir described in Example III. The reservoir was perfused with physiological saline solution and the eluate was collected. The concentration of timolol in the eluate was determined by UV spectroscopy and graphed versus time. The results are presented in the FIGURE.

EXAMPLE VII

Preparation of Drug Delivery Microspheres

The procedure of Example I is followed, using sulfonic acid cationic-exchange resin and ethylcellulose as the coating material. The resulting in microspheres are loaded with gentamycin. The dispersion of the gentamycin-loaded microspheres is placed into to a 500 ml reservoir and the reservoir is perfused with physiological saline solution. The eluate is collected in the concentration of the gentamycin in the eluate is determined.

EXAMPLE VIII

Microspheres are prepared according to Example I, using methacrylic resin as the core material and polycaprolactone as the coating. Sulfisoxazole is loaded into the microspheres as described in Example II and placed into a 500 ml reservoir as described in Example III. The reservoir is perfused with physiological saline solution and the eluate is collected. The concentration of sulfisoxazole is determined in the eluate.

EXAMPLE IX

Microspheres are prepared according to Example I, using dextran polymers as the core and ethylvinyl acetate copolymers as the coating. The polymers are loaded with dexamethasone as described in Example II and placed into a 500 ml reservoir described in Example III. The reservoir is perfused with physiological saline solution and the eluate is collected. The concentration of dexamethasone is determined.

EXAMPLE X

Microspheres are prepared according to Example I, using a cellulosic ion-exchange polymer as the core and polyurethane as the coating. The microspheres are loaded with epinephrine as described in Example II and placed a 500 ml reservoir described in Example III. The reservoir is perfused with physiological saline solution and the eluate is collected. The concentration of epinephrine in the eluate is determined.

What is claimed is:

1. A sustained-release drug delivery composition, comprising an aqueous carrier, and microspheres containing a pharmaceutically active agent, said microspheres comprising a core said core, comprising an ion exchange resin; and a non-crosslinked plymeric coating completely surrounding said core, wherein said coating is selected from the group consisting of a cellulose derivative, a polycaprolactone, a polyurethane, a polymethacrylate, a polyester, ammonio methacrylate copolymers, and copolymers comprising a polycaprolactone, polyurethane, polymethacrylate, or polyester.

2. A method of forming microspheres containing a sustained release drug delivery composition, comprising the steps of:

a) forming a suspension of ion exchange resin particles, said particles having an average diameter of less than about 5 microns, and contacting said suspension with a solution of a water-insoluble, hydrolytically stable polymer in the presence of a surfactant agent, thereby forming a dispersion;

b) removing the solvent from said dispersion to form microparticles, comprising a core, said core comprising said ion exchange resin, and a non-crosslinked polymeric coating, comprising said polymer completely surrounding said core, wherein said coating is selected from the group consisting of a cellulose derivative, a polycaprolactone, a polyurethane, a polymethacrylate, a polyester, ammonio methacrylate copolymers, and copolymers comprising a polycaprolactone, polyurethane, polymethacrylate, or;

c) sterilizing said microparticles;

d) contacting said sterilized microparticles with a sterile aqueous solution of an ionic pharmaceutically active agent, whereby said agent diffuses into said microspheres through said coating and said agent is bound to said ion exchange resin.

* * * * *